US011780870B2

(12) United States Patent
Gan et al.

(10) Patent No.: US 11,780,870 B2
(45) Date of Patent: Oct. 10, 2023

(54) METHOD FOR PREPARING CRYSTALLINE D-PSICOSE

(71) Applicant: SHANDONG BAILONG CHUANGYUAN BIO-TECH CO., LTD., Shandong (CN)

(72) Inventors: Zhaobo Gan, Shandong (CN); Xianbao Shao, Shandong (CN); Fanghua Li, Shandong (CN); Qian Du, Shandong (CN); Xingjing Zhang, Shandong (CN); Shuangshuang Liu, Shandong (CN)

(73) Assignee: SHANDONG BAILONG CHUANGYUAN BIO-TECH CO., LTD., Shandong (CN)

( * ) Notice: Subject to any disclaimer, the term of this patent is extended or adjusted under 35 U.S.C. 154(b) by 0 days.

(21) Appl. No.: 18/011,614

(22) PCT Filed: Dec. 3, 2021

(86) PCT No.: PCT/CN2021/135345
§ 371 (c)(1),
(2) Date: Dec. 20, 2022

(87) PCT Pub. No.: WO2022/117074
PCT Pub. Date: Jun. 9, 2022

(65) Prior Publication Data
US 2023/0287026 A1    Sep. 14, 2023

(30) Foreign Application Priority Data

Dec. 4, 2020 (CN) .......................... 202011406639.1

(51) Int. Cl.
*C07H 1/06* (2006.01)
*C07H 3/02* (2006.01)
(52) U.S. Cl.
CPC ............. *C07H 1/06* (2013.01); *C07H 3/02* (2013.01); *C07B 2200/13* (2013.01)
(58) Field of Classification Search
None
See application file for complete search history.

(56) References Cited

U.S. PATENT DOCUMENTS

| 2011/0237790 A1 | 9/2011 | Lee et al. |
| 2017/0313734 A1 | 11/2017 | Kim et al. |
| 2022/0332745 A1 | 10/2022 | Park et al. |

FOREIGN PATENT DOCUMENTS

| CA | 3090459 A1 | 8/2019 |
| CN | 102250157 A | 11/2011 |
| CN | 109748940 A | 5/2019 |
| CN | 109923120 A | 6/2019 |
| CN | 110627847 A | 12/2019 |
| CN | 110872332 A | 3/2020 |
| CN | 110951806 A | 4/2020 |
| CN | 111741962 A | 10/2020 |
| CN | 112574263 A | 3/2021 |
| WO | 2016064087 A1 | 4/2016 |
| WO | 2020111851 A1 | 6/2020 |

OTHER PUBLICATIONS

CN110872332A, machine translation. (Year: 2020).*
Tianjin Institute of Light Industry, Dalian Institute of Technology, Wuxi Institute of Light Industry, South China Institute of Technology, "Amino Acid Technology" Light Industry Press, Jan. 1983, IBSN No. 15042 1701. (5 Pages Including English Abstract).
Translation of PCT International Search Report for PCT Application No. PCT/CN2021/135345 dated Feb. 24, 2022 (3 pages).

* cited by examiner

*Primary Examiner* — Layla D Berry
(74) *Attorney, Agent, or Firm* — Merchant & Gould P.C.

(57) ABSTRACT

The present application relates to a method for preparing crystalline D-psicose. In the present application, crystalline D-psicose is prepared by means of combining an evaporative crystallization method and a cooling crystallization method, so that the preparation process is simple, the operation is easy, and the crystallization period is short. In the present application, a seed crystal is added when the solid content is relatively low (70-75%) in an evaporative crystallization process, so that the crystallization process is facilitated, the growth speed of the crystal in each direction is more uniform, the whole crystallization period can be shortened, and the energy consumption is reduced; and after the evaporative crystallization is finished, crystal regulation is carried out, so that the crystal size tends to be equalized, the crystal surface grows to be smooth, and the crystal form is perfected. Cooling crystallization is carried out after the crystal regulation, and the cooling frequency of specific cooling intervals is designed in the cooling process according to the metastable region curve of D-psicose. After crystallization by means of the preparation method of the present application is finished, the obtained crystal has a high yield, a narrow crystal size distribution, a smooth crystal surface, a mirror-like surface, good reflectivity and a regular crystal form.

7 Claims, 4 Drawing Sheets

METHOD FOR PREPARING CRYSTALLINE D-PSICOSE

This application is a National Stage Application PCT/CN2021/135345, filed 3 Dec. 2021, which claims benefit of Serial No. 202011406639.1, filed 4 Dec. 2020 in China, and which applications are incorporated herein by reference. To the extent appropriate, a claim of priority is made to each of the above disclosed applications.

TECHNICAL FIELD

The application relates to a method for preparing crystalline D-psicose, belonging to the technical field of functional sugar preparation.

BACKGROUND ART

D-psicose or D-allulose is a six-carbon sugar found in very low levels in the nature and is a differential isomer of the C-3 site of D-fructose. D-psicose is difficult to digest and absorb and provides little energy for vital activities, making it a very useful low-calorie sweetener. In the field of medicine and health, D-psicose inhibits hepatic lipogenic enzyme and intestinal α-glucosidase, thereby reducing the accumulation of body fat and suppressing the rise in blood glucose concentration. Dietary addition of D-psicose reduces the postprandial glycaemic response and improves insulin sensitivity and glucose tolerance. In addition, D-psicose is more effective in scavenging reactive oxygen radicals compared to other rare sugars. In mouse tests, D-psicose is found to prevent testicular damage induced by bis-(2-ethylhexyl)-phthalic acid by inhibiting the production of reactive oxygen species. In addition, D-psicose has a neuroprotective effect against 6-hydroxydopamine-induced apoptosis and also inhibits the expression of the monocyte chemotactic protein MCP-1 induced by high glucose concentrations. This predicts a potential function of D-psicose in the treatment of diseases related to diseases such as neurodegeneration and atherosclerosis, etc.

Chinese patent document CN109748940A (application number 201811470319.5) discloses a method for crystallization of D-psicose from an ethanol solution, which comprises: a purified D-psicose solution is taken and concentrated under reduced pressure to obtain solution I; the concentrated solution I is heated, added with absolute ethanol, concentrated again under reduced pressure to allow the ethanol take away water in the D-psicose solution to obtain an ethanol solution II of D-psicose; the concentrated solution II is added with absolute ethanol, heated until the D-psicose is completely dissolved, then slowly cooled, continuously cooled slowly when the crystal appears, cooled until crystal no longer increases to obtain a mixed solution III; the mixed solution III is solid-liquid separated to obtain a solid IV and a clear liquid V; the solid IV is dried under a reduced pressure to obtain crystalline D-psicose; the clear liquid V is continuously concentrated, and the above steps are repeated to obtain remaining crystalline D-psicose by crystallization.

CONTENTS OF THE INVENTION

The inventors found that the size distribution of crystalline D-psicose obtained by the existing D-psicose crystallization technology is relatively wide.

In view of the deficiencies in the prior art, the present application provides a method for preparing crystalline D-psicose, the size distribution of the crystals of the prepared crystalline D-psicose is narrow, wherein more than 80% of the crystals have sizes in a range of 40 to 60 mesh.

The inventors of the present application studied the properties of D-psicose in metastable zone by plotting D-psicose metastable zone curves. In view of the unique metastable zone curves of D-psicose, the present application adopts specific cooling intervals with specific cooling rates during the cooling crystallization process. Based on this, the crystalline D-psicose prepared by the method of the present application has a narrow size distribution.

The technical solutions of this application are as follows:
In some embodiments, the present application provides a method for preparing crystalline D-psicose, which comprises: (1) evaporative crystallization, (2) crystal regulation, and (3) cooling crystallization, to prepare crystalline D-psicose.

In some embodiments, the present application provides a method for preparing crystalline D-psicose, comprising:
(1) performing evaporative crystallization on a D-psicose syrup;
(2) performing crystal regulation (crystallization regulation) on the product of the previous step;
(3) performing cooling crystallization on the product of the previous step to obtain crystalline D-psicose.

In some embodiments, the evaporative crystallization comprises adding crystal seeds to a D-psicose syrup having a solid mass content of 70~75% (e.g., 70%~71%, 71%~72%, 72%~73%, 73%~74% or 74%~75%) to perform evaporative crystallization.

In some embodiments, the crystal regulation carried out by adding water at the same time as an evaporative crystallization is performed, and a solid mass content is maintained constant during the crystal regulation process. For example, a solid mass content is maintained in a range of 80% to 85%.

In some embodiments, the cooling crystallization adopts a stepped cooling method for crystallization in which a slow cooling is applied in an initial stage and a rapid cooling rate is applied in a later stage.

In some embodiments, the cooling crystallization is performed by applying a stepped cooling method for crystallization, in which a slow cooling is applied in an initial stage and a rapid cooling rate is applied in a later stage; wherein said stepped cooling has the following operations: in a range of 50~41° C., cooling at a rate of 0.1~0.3° C. per hour; in a range of 41~35° C., cooling at a rate of 0.4~0.6° C. per hour; in a range of 35~30° C., cooling at a rate of 0.9~1.1° C. per hour; and the crystallization is finished when temperature is cooled to 30° C.

In some embodiments, the present application provides a method for preparing crystalline D-psicose, comprising the following steps:
(1) evaporative crystallization: providing a D-psicose syrup, in which said D-psicose syrup has a solid mass content of 70~75% (e.g., 70~71%, 71~72%, 72~73%, 73~74% or 74~75%), adding D-psicose crystal seeds, performing evaporative crystallization at 40~50° C., until the D-psicose syrup has a solid mass content of 80~85% (80~81%, 81~82%, 82~83%, 83~84% or 84~85%);
(2) crystal regulation: supplementing water to the D-psicose syrup obtained in step (1), and at the same time continuously performing an evaporative crystallization, consistently maintaining a solid mass content of the D-psicose syrup in a range of 80~85% (80~81%, 81~82%, 82~83%, 83~84% or 84~85%), wherein the crystal regulation is performed for 4~8 h (4~5 h, 5~6 h, 6~7 h or 7~8 h);

(3) cooling crystallization: the D-psicose syrup obtained in step (2) after the completion of the crystal regulation is subjected to stepped cooling crystallization, in which in a range of 50~41° C., cooling at a rate of 0.1~0.3° C. per hour; in a range of 41~35° C., cooling at a rate of 0.4~0.6° C. per hour; in a range of 35~30° C., cooling at a rate of 0.9~1.1° C. per hour; and the crystallization is finished when temperature is cooled to 30° C., then centrifugation, washing and drying are performed to obtain crystalline D-psicose.

In some embodiments, in the evaporative crystallization of step (1), the D-psicose syrup has a solid mass content of 70%~75%, for example 73%~75%, and a purity of ≥95%. A vacuum concentration can be applied to increase the solid mass content of the D-psicose syrup, if the solid mass content of the obtained D-psicose syrup is found to be relatively low. The vacuum concentration is performed at a vacuum degree of −0.05~0 MPa, and at a temperature of 35~40° C.

In some embodiments, in the evaporative crystallization of step (1), the D-psicose crystal seeds is added in an amount of 1~1.5‰ with respect to the mass of the D-psicose syrup with a solid mass content of 70~75%.

In some embodiments, in the evaporative crystallization of step (1), the D-psicose crystal seeds has a size of 250~280 mesh. In the present application, D-psicose crystal seeds having too large size or too small size is not suitable. When the crystal seeds are too large, the number crystal seeds is insufficient, which will lead to the spontaneous nucleation by crystallization, resulting in an excessively large crystal size distribution range, and thus the sizes of the crystals are not uniform. When the crystal seeds are too small, the crystallization process will be very slow.

In some embodiments, in the evaporative crystallization of step (1), the evaporative crystallization is performed at a vacuum degree of −0.05~−0.1 MPa; preferably −0.01 MPa. In terms of the definition of vacuum degree, 1 standard atmospheric pressure is set as the reference zero point, so −0.05 MPa means a pressure that is 0.05 MPa lower than 1 standard atmospheric pressure.

In some embodiments, in the evaporative crystallization of step (1), the evaporative crystallization is performed until the D-psicose syrup has a solid mass content of 81~83%.

In some embodiments, in the crystal regulation of step (2), the solid mass content of the D-psicose syrup is constantly maintained in a range of 82% and 83%.

The purpose of step (2) of the present application is to regulate the crystalline, so that the sizes of the crystals are becoming uniform, and at the same time, the surface of the crystals grows to be smooth, and the morphology of the crystals is improved; wherein, the conditions for evaporative crystallization during the crystal regulation are the same as the conditions for evaporative crystallization in step (1). After the completion of the crystal regulation, the crystallization yield rate can reach more than 10%, and more than 80% of the crystals have sizes in a range of 80~100 mesh.

In some embodiments, in the cooling crystallization of step (3), a stirring with a speed of 100~150 rpm is applied; preferably a stirring with a speed of 100 rpm is applied.

In some embodiments, in the cooling crystallization of step (3), the stepped cooling is performed as follows: in a range of 50~41° C., cooling at a rate of 0.2° C. per hour; in a range of 41~35° C., cooling at a rate of 0.5° C. per hour; in a range of 35~30° C., cooling at a rate of 1° C. per hour.

The present application creatively studied the metastable zone curves of D-psicose (as shown in FIG. 12). It can be seen from the figure that with the increase of temperature, the width of the metastable zone of D-psicose is gradually narrowed down. Therefore, at a higher temperature (such as 35~50° C.), if the cooling rate is too fast during cooling crystallization, the spontaneous nucleation will be induced, resulting uneven size distribution of the crystals.

In the cooling crystallization of step (3) of the present application, constant cooling rate is not adopted, instead, cooling rates for specific cooling intervals are designed according to the metastable zone curves of D-psicose. The D-psicose metastable zone curves are characterized by a narrow metastable zone at high temperature and a wide metastable zone at low temperature.

Therefore, the cooling rate for cooling crystallization is slow in initial stages and fast in later stages, which can avoid phenomenon of the spontaneous nucleation and uneven sizes of the crystals caused by too fast cooling rate in initial stages, and phenomenon of slow crystal growth and low yield caused by too slow cooling rate in later stages. After the completion of the crystallization, the yield rate of crystalline D-psicose was measured to be more than 55%, and more than 80% of the crystals have sizes in a range of 40 and 60 mesh.

In some embodiments, unless otherwise specified, % refers to weight percentage.

In some embodiments, "D-psicose crystal" is used interchangeably with "crystalline D-psicose", and both have the same meaning.

In some embodiments, D-psicose syrup is an aqueous solution of D-psicose.

Beneficial Effect

One or more embodiments of the present application have one or more of the following beneficial effects:

1. The method for preparing crystalline D-psicose in the present application adopts a method combining an evaporative crystallization and a cooling crystallization. The method is simple in preparation process, easy to operate, and short in crystallization period (e.g., there is no need to perform repeated heating-cooling processes for many times); the method has reduced production cost and simplified preparation process (e.g., no organic solvent needs to be added).
2. In the present invention, crystal seeds are added during the process of evaporative crystallization when the solid mass content is relatively low (70~75%). At this time, the viscosity of the D-psicose syrup is low, and the mass transfer performance of syrup is good, which is conducive to molecular movement. Besides, there is less resistance for the molecules to approach crystal nuclei, which is conducive to the crystallization process, making crystals have more uniform growth rate in all directions. Further, the addition of crystal seeds at this time can shorten the entire crystallization period and reduce energy consumption. Since the crystallization starts from a low solid mass content, the yield rate of the obtained crystals is higher.
3. In the present application, the sizes of the crystal seeds are optimized, and the optimized sizes of the crystal seeds are in a range 250~280 mesh. If the crystal seeds are too large, the number of crystal seeds is insufficient, which will lead to spontaneous nucleation during crystallization, resulting in an excessively wide size distribution of the crystals and crystals with uneven sizes; if the crystal seeds are too small, a slow crystallization process is likely to occur.

4. In the present application, after the evaporative crystallization, cooling crystallization is not immediately performed, but a crystal regulation is performed. The crystal regulation makes the sizes of the crystals become uniform, and meanwhile, the surface of the crystals grows to be smooth, and the morphology of the crystals is improved; after the completion of the crystal regulation, the crystallization yield rate can reach more than 10%, and more than 80% of the crystals have sizes in a range of 80~100 mesh.

5. In the present application, specific cooling interval and cooling rate are designed according to the metastable zone curves of D-psicose during the cooling process. The cooling crystallization helps to obtain crystalline D-psicose with a narrow size distribution. The phenomena of spontaneous nucleation and uneven size distribution of the crystals caused by too fast cooling in initial stages are avoided, and the phenomena of slow crystal growth, low yield, long period and high energy consumption caused by too slow cooling in later stages are also avoided.

6. After the completion of crystallization according to the preparation method of the present application, the obtained crystals have a high yield rate, the yield rate of crystalline D-psicose can reach more than 55%, the size distribution of the crystals is narrow, the sizes of more than 80% crystals are in the range of 40~60 mesh, the crystal has a smooth, mirror-like surface, with good reflectivity, and has a regular crystal shape. This technical effect exceeds the expectations of those skilled in the art, which is an unexpected technical effect.

SPECIFIC MODELS FOR CARRYING OUT THE INVENTION

The technical solutions of the present application will be further described below with reference to the examples, but the protection scope of the present application is not limited to this. The materials or instruments involved in the examples are ordinary commercial products in the art unless otherwise specified; the experimental operations involved in the examples are conventional experimental operations in the art unless otherwise specified.

The D-psicose syrup used in the examples could be obtained by one or a combination of chemical synthesis or biocatalytic conversion.

Unless otherwise specified, the % used below all represent the weight percentage.

In the following embodiments, the test method of size distribution of the crystals were obtained by step-by-step sieving using 20 mesh, 40 mesh, 60 mesh, 80 mesh and 100 mesh screen.

In some embodiments, the size of mesh has meanings known in the art, for example, GB or ISO standards in the art could be referred to, for example, GB6005-85, IS0565-1983 standards could be referred to.

Example 1

Figure 1:
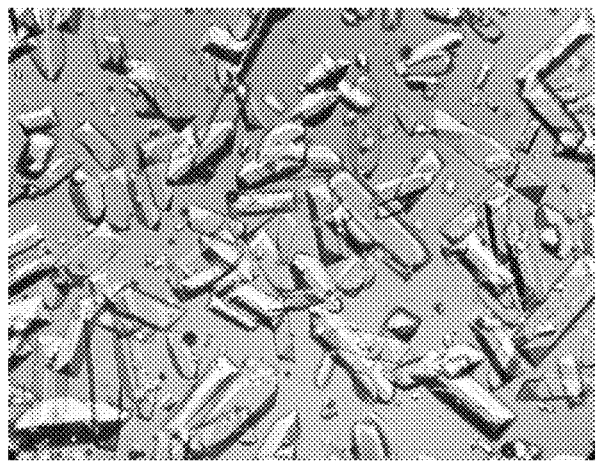
FIG. 1 shows a microscope photograph of the obtained crystals after the completion of crystal regulation in Example 1.

A method for preparing crystalline D-psicose, comprised the steps of:
(1) evaporative crystallization: a D-psicose syrup (aqueous solution of D-psicose) was provided, the D-psicose syrup had a solid mass content of 73%, a purity of ≥95%, D-psicose crystal seeds were added, the amount of the D-psicose crystal seeds added was 1‰ of the D-psicose syrup, the sizes of the D-psicose crystal seeds were in a range of 250 and 280 mesh, evaporative crystallization was performed at 41° C., with a vacuum degree of −0.01 MPa, until the D-psicose syrup had a solid mass content of 81%;
(2) crystal regulation: water was supplemented to the D-psicose syrup obtained in step (1), and an evaporative crystallization was continuously performed at 41° C., with a vacuum degree of −0.01 MPa, the solid mass content of the D-psicose syrup was maintained in a range of 82~83%, and crystal regulation was performed for 4 h; After the completion of the crystal regulation, crystals were obtained and a microscope photograph (100 times) of the obtained crystals was shown in FIG. 1. The sizes of the crystals become uniform, the surface of the crystals grew to be smooth, and the crystallization yield rate of D-psicose was 12.34%. The size distribution of the obtained crystals was shown in the following table, indicating that 81.32% of the crystals have sizes in a range of 80~100 mesh:

TABLE 1 size distribution of the crystals after crystal regulation in Example 1

| Sizes of the crystals | Distribution |
|---|---|
| 20 mesh or more | — |
| 20-40 mesh | 0.18% |

TABLE 1-continued size distribution of the crystals after crystal regulation in Example 1

| Sizes of the crystals | Distribution |
|---|---|
| 40-60 mesh | 0.52% |
| 60-80 mesh | 14.35% |
| 80-100 mesh | 81.32% |
| below 100 mesh | 3.63% |

(3) Cooling crystallization: the D-psicose syrup obtained after the completion of the crystal regulation in step (2) was subjected to stepped cooling crystallization, in which in a range of 41~35° C., the temperature was lowered by 0.5° C. per hour; in a range of 35~30° C., the temperature was lowered by 1° C. per hour; during the cooling crystallization process, a stir was applied with a stirring speed of 100 rpm; the crystallization was finished when the temperature was cooled to 30° C., then centrifugation, washing and drying were performed to obtain crystalline D-psicose.

Figure 2:
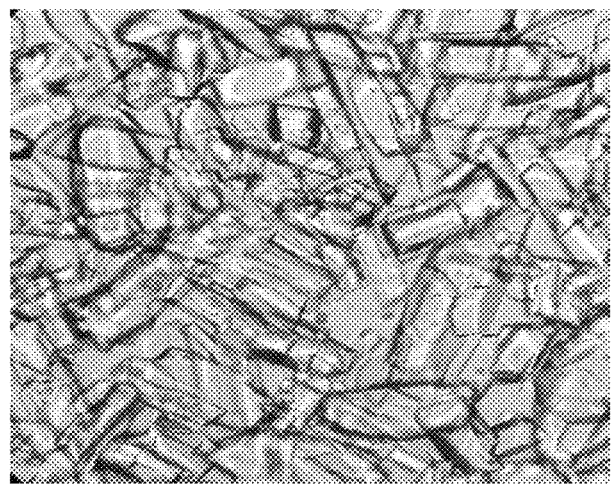
FIG. 2 shows a microscope photograph of the obtained crystals after the completion of crystallization in Example 1.

After the completion of crystallization, a microscope photograph (100 times) of the obtained crystals were shown in FIG. 2, indicating that the size distribution of the crystals was narrow, the crystals had smooth mirror-like surface, good reflectivity, and regular crystal shape. The yield rate of crystalline D-psicose was measured to be 58.31%, the purity was 99.62%, the size distribution of the obtained crystals was shown in the table below, and 28.31% of the crystals have sizes in a range of 40~60 mesh:

TABLE 2 size distribution of the crystals after crystallization in Example 1

| Sizes of the crystals | Distribution |
|---|---|
| 20 mesh or more | 0.72% |
| 20-40 mesh | 5.98% |
| 40-60 mesh | 82.31% |
| 60-80 mesh | 8.67% |
| 80-100 mesh | 2.32% |
| below 100 mesh | — |

Example 2

Figure 3:
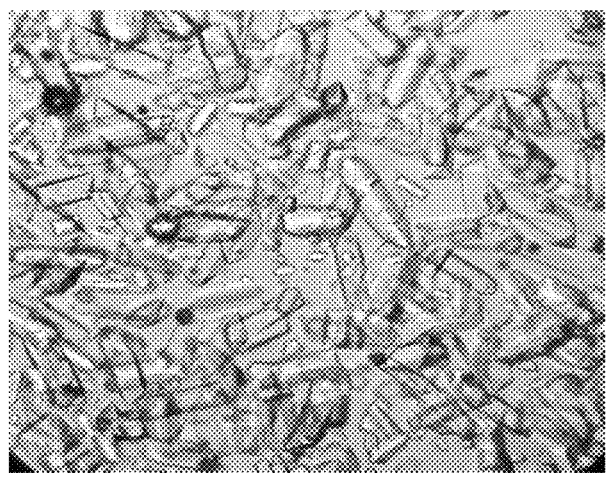
FIG. 3 shows a microscope photograph of the obtained crystals after the completion of crystal regulation in Example 2.

A method for preparing crystalline D-psicose, comprised the steps of:
(1) evaporative crystallization: a D-psicose syrup was provided, the D-psicose syrup had a solid mass content of 74%, a purity of ≥95%, D-psicose crystal seeds were added, the amount of the D-psicose crystal seeds added was 1.2‰ of the D-psicose syrup, the size of the D-psicose crystal seeds were in a range of 250 and 280 mesh, evaporative crystallization was performed at 45° C. with a vacuum degree of −0.01 MPa, until the D-psicose syrup had a solid mass content of 82%;
(2) crystal regulation: water was supplemented to the D-psicose syrup obtained in step (1), and an evaporative crystallization was continuously performed at 45° C. with a vacuum degree of −0.01 MPa, and the solid mass content of the D-psicose syrup was maintained in a range of 82~83%, and crystal regulation was performed for 6 h;

After the completion of the crystal regulation, crystals were obtained and a microscope photograph (100 times) of the obtained crystals was shown in FIG. 3. The sizes of the crystals became uniform, the surface of the crystals grew to be smooth, and the crystallization yield rate of D-psicose was measured to be 11.60%. The size distribution of the obtained crystals was shown in the following table, indicating that 81.56% of the crystals have sizes in a range of 80~100 mesh:

TABLE 3 size distribution of the crystals after crystallization in Example 2

| Sizes of the crystals | Distribution |
|---|---|
| 20 mesh or more | — |
| 20-40 mesh | 0.71% |
| 40-60 mesh | 2.64% |
| 60-80 mesh | 10.53% |
| 80-100 mesh | 81.56% |
| below 100 mesh | 4.56% |

(3) Cooling crystallization: the D-psicose syrup obtained after the completion of the crystal regulation in step (2) was subjected to stepped cooling crystallization, wherein in a range of 45~41° C., the temperature was lowered by 0.2° C. per hour; in a range of 41~35° C., the temperature was lowered by 0.5° C. per hour; in a range of 35~30° C., the temperature was lowered by 1° C. per hour; during the cooling crystallization process, a stir was applied with a stirring speed of 100 rpm; the crystallization was finished when the temperature was cooled to 30° C., then centrifugation, washing and drying were performed to obtain crystalline D-psicose.

Figure 4:
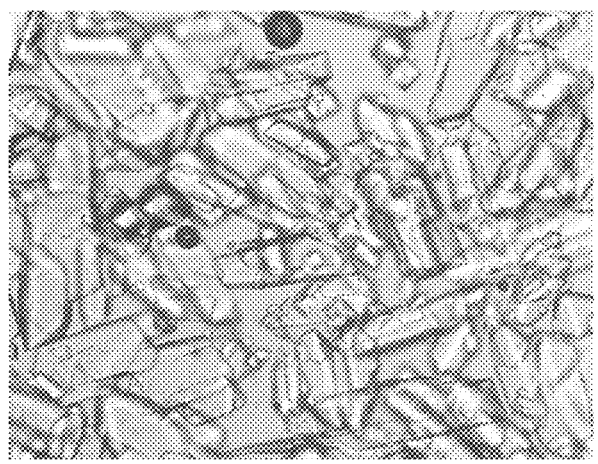
FIG. 4 shows a microscope photograph of the obtained crystals after the completion of crystallization in Example 2.

After the completion of crystallization, a microscope photograph (100 times) of the obtained crystals was shown in FIG. 4, indicating that the size distribution of the crystals was narrow, the crystals had smooth mirror-like surface, good reflectivity, and regular crystal shape. The yield rate of crystalline D-psicose was measured to be 57.89%, the purity was 99.58%, the size distribution of the obtained crystals was shown in the table below, and the 82.11% of the crystals have sizes in a range of 40~60 mesh:

TABLE 4 size distribution of the crystals after crystallization in Example 2

| Sizes of the crystals | Distribution |
|---|---|
| 20 mesh or more | 0.87% |
| 20-40 mesh | 6.43% |
| 40-60 mesh | 82.11% |
| 60-80 mesh | 8.46% |
| 80-100 mesh | 2.13% |
| below 100 mesh | — |

Example 3

Figure 5:
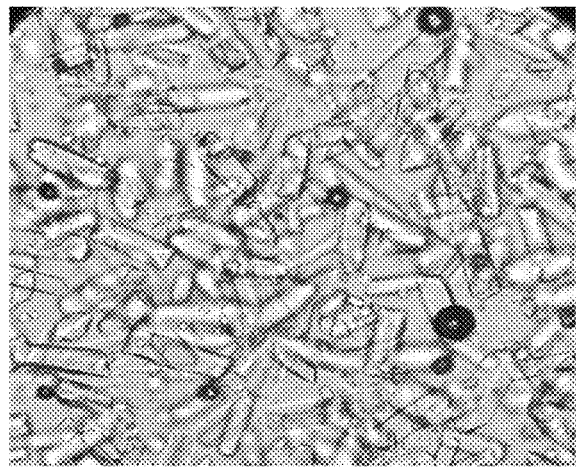
FIG. 5 shows a microscope photograph of the obtained crystals after the completion of crystal regulation in Example 3.

A method for preparing crystalline D-psicose, comprised the steps of:
(1) Evaporative crystallization: a D-psicose syrup was provided, the D-psicose syrup had a solid mass content of 75%, a purity of ≥95%, D-psicose crystal seeds were added, the amount of the D-psicose crystal seeds added was 1.5‰ of the D-psicose syrup, the size of the D-psicose crystal seeds were in a range of 250 and 280 mesh, evaporative crystallization was performed at 50° C. with a vacuum degree of −0.01 MPa, until the D-psicose syrup had a solid mass content of 83%;
(2) Crystal regulation: water was supplemented to the D-psicose syrup obtained in step (1), and the evaporative crystallization was continuously performed at 50° C. with a vacuum degree of −0.01 MPa, and the solid mass content of the D-psicose syrup was maintained in a range of 82~83%, and crystal regulation was performed for 8 h;

After the completion of the crystal regulation, crystals were obtained and a microscope photograph (100 times) of the obtained crystals was shown in FIG. 5. The sizes of the crystals became uniform, the surface of the crystals grew to be smooth, and the crystallization yield rate of D-psicose was measured to be 10.92%. The size distribution of the obtained crystals was shown in the following table, indicating that 80.69% of the crystals have sizes in a range of 80~100 mesh:

TABLE 5 size distribution of the crystals after crystallization in Example 3

| Sizes of the crystals | Distribution |
| --- | --- |
| 20 mesh or more | — |
| 20-40 mesh | 1.51% |
| 40-60 mesh | 3.23% |
| 60-80 mesh | 8.86% |
| 80-100 mesh | 80.69% |
| below 100 mesh | 5.71% |

(3) Cooling crystallization: the D-psicose syrup obtained after the completion of the crystal regulation in step (2) was subjected to stepped cooling crystallization, in which in a range of 50~41° C., the temperature was lowered by 0.2° C. per hour; in a range of 41~35° C., the temperature was lowered by 0.5° C. per hour; in a range of 35~30° C., the temperature was lowered by 1° C. per hour; during the cooling crystallization process, a stir was applied with a stirring speed of 100 rpm; the crystallization was finished when the temperature was cooled to 30° C., then centrifugation, washing and drying were performed to obtain crystalline D-psicose.

Figure 6:
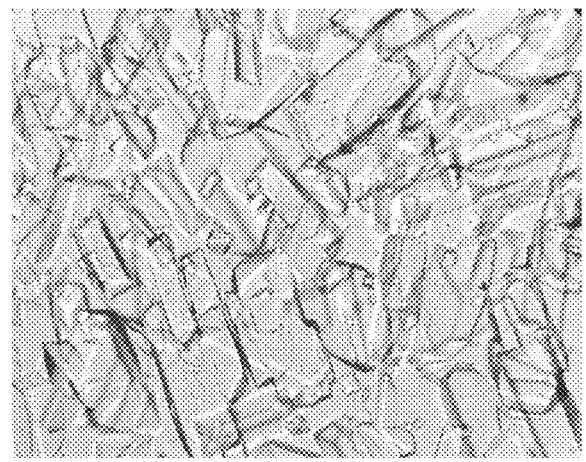
FIG. 6 shows a microscope photograph of the obtained crystals after the completion of crystallization in Example 3.

After the completion of crystallization, a microscope photograph (100 times) of the obtained crystals was shown in FIG. 6, indicating that the size distribution of the crystals was narrow, the crystals had smooth mirror-like surface, good reflectivity, and regular crystal shape. The yield rate of crystalline D-psicose was measured to be 56.45%, the purity was 99.64%, the size distribution of the obtained crystals was shown in the table below, and the size of 80.79% of the crystals have sizes in a range of 40~60 mesh:

TABLE 6 size distribution of the crystals after crystallization in Example 3

| Sizes of the crystals | Distribution |
| --- | --- |
| 20 mesh or more | 0.75% |
| 20-40 mesh | 5.68% |
| 40-60 mesh | 80.79% |
| 60-80 mesh | 10.11% |
| 80-100 mesh | 2.67% |
| below 100 mesh | — |

Comparative Example 1

The crystallization of D-psicose was carried out according to the preparation method of Example 2, the difference lied in that the D-psicose crystal seeds were added when the D-psicose syrup in step (1) had a solid mass content of 80%, which was obtained by being concentrated at 35~40° C. with a vacuum degree of −0.01 MPa. Other steps and operations were the same as in Example 2.

Figure 7:
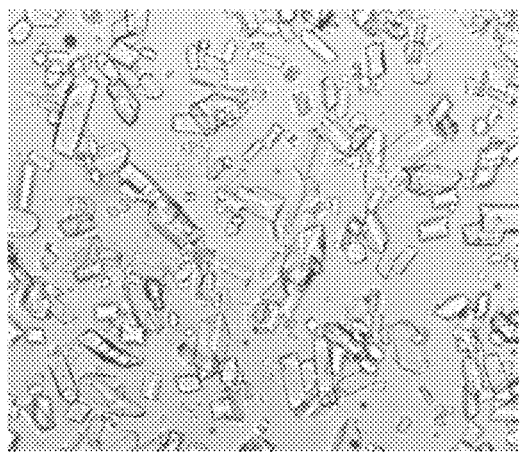
FIG. 7 shows a microscope photograph of the obtained crystals after the completion of crystallization in Comparative Example 1.

After the completion of crystallization, crystals were obtained and a microscope photograph (100 times) of the obtained crystals was shown in FIG. 7. The yield rate of the crystalline D-psicose was measured to be 47.62%, and the purity was 98.97%. The size distribution of the obtained crystals was shown in the following table, the sizes of the crystals were mostly distributed in ranges of 40~60 mesh and 60~80 mesh, also in other ranges of sizes, and the size distribution of the crystals was nonconcentrated:

TABLE 7 size distribution of the crystals after crystallization in Comparative Example 1

| Sizes of the crystals | Distribution |
| --- | --- |
| 20 mesh or more | 3.06% |
| 20-40 mesh | 8.24% |
| 40-60 mesh | 45.16% |
| 60-80 mesh | 30.62% |
| 80-100 mesh | 8.71% |
| below 100 mesh | 4.21% |

Comparative Example 2

The crystallization of D-psicose was carried out according to the preparation method of Example 2, the difference lied in that the sizes of the D-psicose crystal seeds added in step (1) were in a range of 180~200 mesh, and other steps and operations were the same as those of Example 2.

Figure 8:
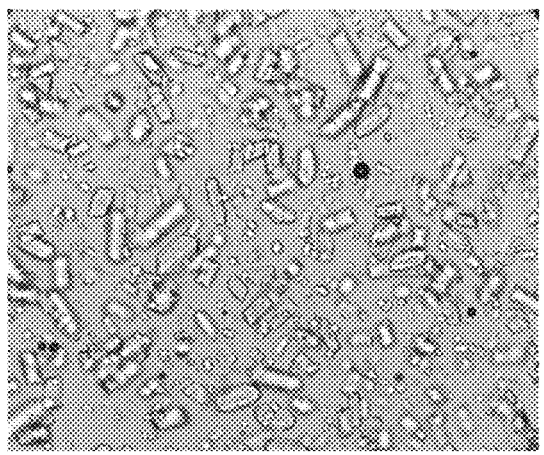
FIG. 8 shows a microscope photograph of the obtained crystals after the completion of crystallization in Comparative Example 2.

After the crystallization, crystals were obtained and a microscope photograph (100 times) of the obtained crystals was shown in FIG. 8. The yield rate of the crystalline D-psicose was measured to be 41.54%, and the purity was 98.83%. The size distribution of the obtained crystals was shown in the following table, and the sizes of the crystals were mostly distributed in ranges of 40~60 mesh, 60~80 mesh and 80~100 mesh, also in other size ranges, the size distribution of the crystals was nonconcentrated, and the yield rate was low:

TABLE 8 size distribution of the crystals after crystallization in Comparative Example 2

| Sizes of the crystals | Distribution |
| --- | --- |
| 20 mesh or more | 5.13% |
| 20-40 mesh | 9.36% |
| 40-60 mesh | 23.16% |
| 60-80 mesh | 35.48% |
| 80-100 mesh | 17.23% |
| below 100 mesh | 9.64% |

Comparative Example 3

The crystallization of D-psicose was carried out according to the preparation method of Example 2, the difference lied in that the size of the D-psicose crystal seeds added in step (1) was in a range of 300 to 320 mesh, and other steps and operations were the same as those of Example 2.

Figure 9:
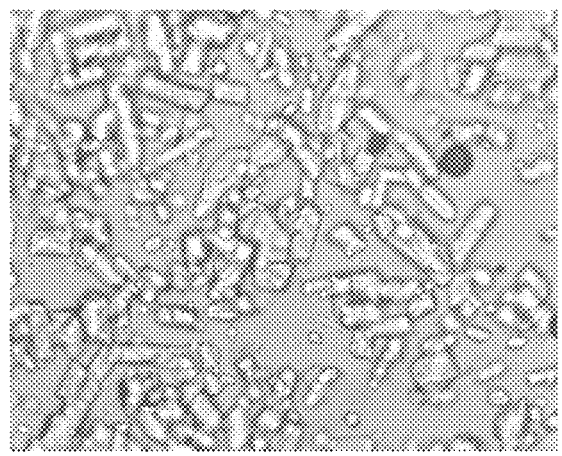
FIG. 9 shows a microscope photograph of the obtained crystals after the completion of crystallization in Comparative Example 3.

After the crystallization, crystals were obtained and a microscope photograph (100 times) of the obtained crystals was shown in FIG. 9. The yield rate of the crystalline D-psicose was measured to be 41.6%, and the purity was 98.91%. The size distribution of the obtained crystals was shown in the following table, and the sizes of the crystals were mostly distributed in a range of 40~60 mesh, 60~80 mesh, 80~100 mesh and below 100 mesh, and also in other size ranges, the size distribution of the crystals was non-concentrated, the form of crystals was small, and the yield rate was low:

TABLE 9 size distribution of the crystals after crystallization in Comparative Example 3

| Sizes of the crystals | Distribution |
|---|---|
| 20 mesh or more | 0.74% |
| 20-40 mesh | 5.48% |
| 40-60 mesh | 28.44% |
| 60-80 mesh | 31.45% |
| 80-100 mesh | 20.68% |
| below 100 mesh | 13.21% |

Comparative Example 4

The crystallization of D-psicose was carried out according to the preparation method of Example 2, the difference lied in that step (2) was omitted, that was, the crystal regulation process was not performed, and other steps and operations were the same as those of Example 2.

Figure 10:
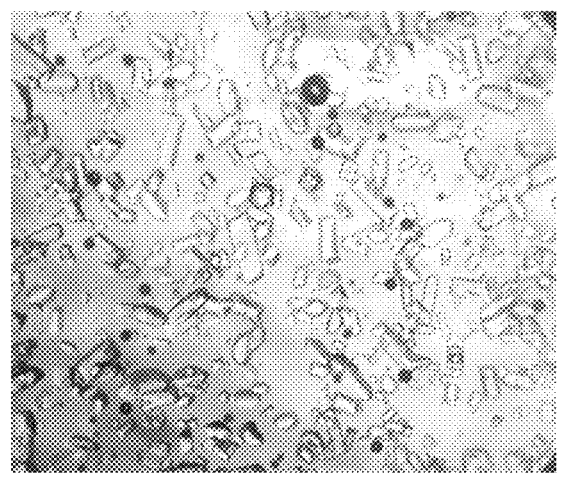
FIG. 10 shows a microscope photograph of the obtained crystals after the completion of crystallization in Comparative Example 4.

After the crystallization, crystals were obtained and a microscope photograph (100 times) of the obtained crystals was shown in FIG. 10. The yield rate of the crystalline D-psicose was measured to be 45.38%, and the purity was 99.03%. The size distribution of the obtained crystals was shown in the following table, and the sizes of the crystals were mostly distributed in a range of 40~60 mesh, 60~80 mesh, 80~100 mesh and below 100 mesh, and also in other size ranges, the size distribution of the crystals was non-concentrated, and the form of crystals was small:

TABLE 10 size distribution of the crystals after crystallization in Comparative Example 4

| Sizes of the crystals | Distribution |
|---|---|
| 20 mesh or more | 1.44% |
| 20-40 mesh | 7.69% |
| 40-60 mesh | 23.85% |
| 60-80 mesh | 28.87% |
| 80-100 mesh | 24.67% |
| below 100 mesh | 13.48% |

Comparative Example 5

The crystallization of D-psicose was carried out according to the preparation method of Example 2, the difference lied in that, the stepped cooling method was not adopted in step (3), instead, the cooling crystallization was carried out in a uniform manner. The temperature was uniformly lowered from 45° C. to 30° C., the temperature was lowered by 1° C. per hour, and other steps and operations were the same as those of Example 2.

Figure 11:
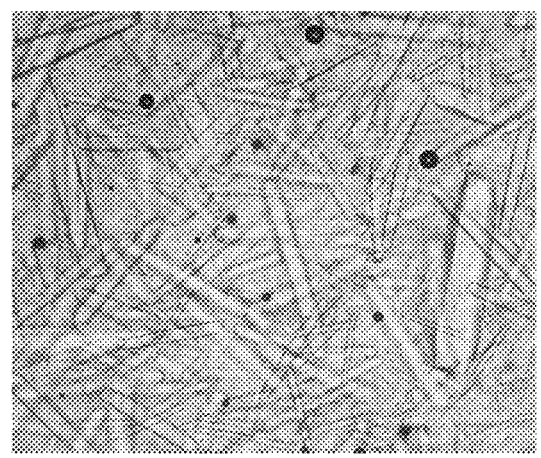
FIG. 11 shows a microscope photograph of the obtained crystals after the completion of crystallization in Comparative Example 5.

After the crystallization, crystals were obtained and a microscope photograph (100 times) of the obtained crystals was shown in FIG. 11. The yield rate of the crystalline D-psicose was measured to be 38.94%, and the purity was 98.77%. The size distribution of the obtained crystals was shown in the following table, and the sizes of the crystals were mostly distributed in a range of 40~60 mesh, 60~80 mesh, 80~100 mesh and below 100 mesh, and also in other size ranges, the size distribution of the crystals was non-concentrated, the form of crystals was small, and the yield rate was low:

TABLE 11 size distribution of the crystals after crystallization in Comparative Example 5

| Sizes of the crystals | Distribution |
|---|---|
| 20 mesh or more | 0.98% |
| 20-40 mesh | 3.1% |
| 40-60 mesh | 12.16% |
| 60-80 mesh | 27.37% |
| 80-100 mesh | 38.21% |
| below 100 mesh | 18.18% |

Experiment: Determination of Curve of Metastable Zone of D-Psicose

Detection Method:

Determination of lower limit of metastable zone of D-psicose syrup: the lower limit of metastable zone was the saturation concentration curve. At a certain temperature, D-psicose powder was added to water until it did not dissolve, and then the solid mass content in the supernatant after centrifugation was measured, which was the saturation concentration at the temperature. Taking the temperature as the abscissa and the saturation concentration as the ordinate, the lower limit of the metastable zone was obtained.

Determination of upper limit of metastable zone of D-psicose syrup: the saturated solution at a certain temperature was cooled at a cooling rate of 0.2° C./h with a stirring speed of 50 rpm. When crystals were precipitated out from the solution, the solid mass content in the supernatant was measured by centrifugation, and the temperature at this time was recorded, which was the upper limit of the supersaturation concentration at this temperature. Taking the temperature as the abscissa and the upper limit of the supersaturation concentration as the ordinate, the upper limit of the metastable zone was obtained.

Figure 12:
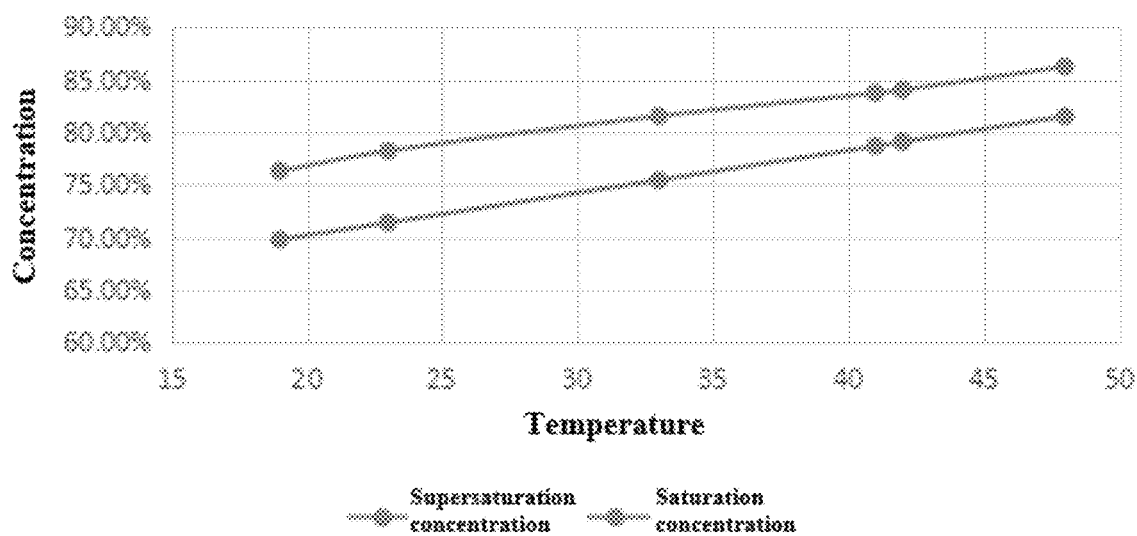
FIG. 12 shows a graph of the metastable zone curves of D-psicose, in the figure, the upper curve is the supersaturation curve, and the lower curve is the saturation curve.

The curves of metastable zone of D-psicose as measured according to the above measuring method were shown in FIG. 12. It could be seen from the figure that with the increase of temperature, the width of the metastable zone of D-psicose gradually narrowed down. Therefore, at a higher temperature, such as 35~50° C., a cooling rate that was too fast during the cooling crystallization will lead to spontaneous nucleation of D-psicose and uneven size distribution of the crystals.

Experimental Results

From the experimental data of Examples 1 to 3 and Comparative Examples 1 to 5, the following experimental conclusions can be obtained.

During the crystallization, the cooling interval and cooling rate are important parameters. The inventors of the present application have studied the properties of the metastable zone of D-psicose by plotting the D-psicose metastable zone curves. It can be seen from the curves of the metastable zone that as the temperature increases, the width of the metastable zone of D-psicose gradually narrows down. Therefore, at a higher temperature, such as 35~50° C., a cooling rate during the cooling crystallization that was too fast would lead to the spontaneous nucleation of D-psicose, and the sizes of the crystals would not be uniform. Therefore, the present application adopted specific cooling intervals with specific cooling rates in the cooling crystallization process for the unique metastable zone curves of D-psicose. The crystalline D-psicose obtained by the cooling crystallization scheme of the present application has narrow size distribution, as well as high efficiency, high yield and high purity of crystallization.

The cooling crystallization scheme of the present application avoids the phenomena of spontaneous nucleation and uneven size distribution of the crystals caused by too fast cooling in an initial stage, and also avoids the phenomena of slow crystal growth, low yield rate, long period and high energy consumption caused by too slow cooling in a later stage. If the scheme of the present application is not adopted, for example, in Comparative Example 5, a uniform cooling method was adopted to conduct the cooling crystallization, the temperature was uniformly lowered from 45° C. to 30° C. at a cooling rate 1° C. per hour, the yield rate of D-psicose was measured to be 38.94%, the purity was 98.77%, and the size of the obtained crystals were mostly distributed in ranges of 40~60 mesh, 60~80 mesh, 80~100 mesh and below 100 mesh, and also in other size ranges, the size distribution of the crystals was nonconcentrated, the form of crystals was small, and the yield rate was low.

During crystallization, the solid mass content of the initial D-psicose syrupy is an important parameter. In the present application, it was found through research that in the process of evaporative crystallization, when the crystal seeds were added at a relative low solid mass content (70~75%), the D-psicose syrup under this condition had a low viscosity, the transfer performance of materials was good, which was conducive to the movement of molecules, and the resistance for the molecules to approach the crystal nucleus was small, which was conducive to the crystallization process. The crystal growth rate was more uniform at various directions. The addition of crystal seeds at this time could shorten the entire crystallization period and reduce energy consumption; since the crystallization started from a low solid mass content, the obtained crystals yield rate was higher. If the scheme of the present application was not adopted, for example, in Comparative Example 1, the crystal seeds were added to carry out crystallization when the solid mass content of the D-psicose syrup was 80%, the yield rate of crystalline D-psicose was measured to be 47.62%, the purity was 98.97%, the size distribution of the obtained crystals was nonconcentrated, and the invention purpose of the present application could not be achieved.

During the crystallization, the size of the D-psicose crystal seeds is an important parameter. The size of the crystal seeds is preferably in a range of 250 to 280 mesh. When the crystallization is performed by adopting crystal seeds having a size located in this range, the obtained product has a narrow size distribution, uniform crystal sizes, fast crystallization speed and high production efficiency.

What is claimed is:

1. A preparation method of crystalline D-psicose, wherein, successively performing evaporative crystallization, crystal regulation, and cooling crystallization to obtain crystalline D-psicose;

said evaporative crystallization comprises adding crystal seeds when a solid mass content is 70~75% to perform an evaporative crystallization;

said cooling crystallization is performed by applying a stepped cooling having a slow cooling rate in an initial stage and a rapid cooling rate in a later stage; wherein said stepped cooling has following operations: in a range of 50~41° C., cooling at a rate of 0.1~0.3° C. per hour; in a range of 41~35° C., cooling at a rate of 0.4~0.6° C. per hour; in a range of 35~30° C., cooling at a rate of 0.9~1.1° C. per hour; and the crystallization is finished when temperature is cooled to 30° C.; and said crystal regulation is carried out by adding water at the same time as an evaporative crystallization is performed, and a solid mass content is maintained constant during the crystal regulation process.

2. The preparation method according to claim 1, wherein, specifically comprises the following steps:

(a) evaporative crystallization: providing a D-psicose syrup, in which said D-psicose syrup has a solid mass content of 70~75%, adding D-psicose crystal seeds, performing evaporative crystallization at 40~50° C., until the D-psicose syrup has a solid mass content of 80~85%;

(b) crystal regulation: supplementing water to the D-psicose syrup obtained in step (a), and at the same time continuously performing an evaporative crystallization, consistently maintaining a solid mass content of the D-psicose syrup in a range of 80~85%, wherein the crystal regulation is performed for 4~8 h;

(c) cooling crystallization: the D-psicose syrup obtained in step (b) after the completion of the crystal regulation is subjected to stepped cooling crystallization, in which in a range of 50~41° C., cooling at a rate of 0.1~0.3° C. per hour; in a range of 41~35° C., cooling at a rate of 0.4~0.6° C. per hour; in a range of 35~30° C., cooling at a rate of 0.9~1.1° C. per hour; and the crystallization is finished when temperature is cooled to 30° C., then performing centrifugation, washing and drying to obtain crystalline D-psicose.

3. The preparation method according to claim 2, wherein, said D-psicose syrup in step (a) has a solid mass content of 73~75%, and a purity of ≥95%.

4. The preparation method according to claim 2, B wherein, said D-psicose crystal seeds in step (a) is added in an amount of 1~1.5‰ with respect to the mass of the D-psicose syrup having a solid mass content of 70~75%.

5. The preparation method according to claim 2, wherein, said D-psicose crystal seeds in step (a) have sizes in a range of 250~280 mesh.

6. The preparation method according to claim 2, wherein, said evaporative crystallization in step (a) is performed at a vacuum degree of −0.05~−0.1 MPa.

7. The preparation method according to claim 2, wherein, in said cooling crystallization process in step (c) a stirring with a speed of 100~150 rpm is applied.

* * * * *